US00PP15915P2

(12) United States Plant Patent
Parthasarathy et al.

(10) Patent No.: US PP15,915 P2
(45) Date of Patent: Aug. 9, 2005

(54) ***AGLAONEMA* PLANT NAMED 'STERLING'**

(50) Latin Name: *Aglaonema hybrida*
Varietal Denomination: Sterling

(75) Inventors: Gopalaswamy Parthasarathy, Bangalore (IN); Parthasarathy Mukundan, Bangalore (IN)

(73) Assignee: K.S.G's Farm & Nursery, Alwarpet (IN)

( * ) Notice: Subject to any disclaimer, the term of this patent is extended or adjusted under 35 U.S.C. 154(b) by 8 days.

(21) Appl. No.: 10/878,434

(22) Filed: Jun. 28, 2004

(51) Int. Cl.[7] ..... A01H 5/00
(52) U.S. Cl. ..... Plt./376

(58) Field of Search ..... Plt./376

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Aglaonema* plant named 'Sterling', characterized by its upright and outwardly arching plant form; vigorous growth habit; freely clumping habit; full, dense and bushy plant appearance; undulate lanceolate leaves with acuminate apices; leaves positioned roughly horizontally; unique leaf coloration; upper leaf surfaces lustrous silvery gray green-colored with sparse lighter silvery gray green-colored flecks and chevrons; lower leaf surfaces medium green-colored; green-colored leaf petioles with sparse and random pale yellow-colored spots and streaks; and tolerance to low temperatures.

1 Drawing Sheet

Botanical classification/cultivar denomination: *Aglaonema hybrida* cultivar Sterling.

BACKGROUND OF THE INVENTION

The present Invention relates to a new and distinct cultivar of *Aglaonema* plant, botanically known as *Aglaonema hybrida* and hereinafter referred to by the name 'Sterling'.

The new *Aglaonema* is the result of a planned breeding program conducted by the Inventors in Chamrajpet, Bangalore, India. The objective of the breeding program is to create new vigorous *Aglaonema* cultivars with compact and dense plant habit, unique leaf coloration, interesting leaf shapes, resistance to pathogens and pests common to *Aglaonemas* and tolerance to low temperatures.

The new *Aglaonema* originated from a cross-pollination made by the Inventors on Apr. 24, 1984 of the *Aglaonema commutatum* cultivar Malay Lady, not patented, as the female, or seed, parent with a proprietary selection of *Aglaonema hybrida* identified as code number KSG Hybrid 85-22-1, not patented, as the male, or pollen, parent. The new *Aglaonema* was discovered and selected by the Inventors in 1988 as a single plant within the progeny of the stated cross-pollination in a controlled environment in Chamrajpet, Bangalore, India. The new *Aglaonema* was selected on the basis of its plant habit, leaf shape and uniquely colored foliage.

Asexual propagation of the new cultivar by divisions since September, 1989 in a controlled environment in Chamrajpet, Bangalore, India, has shown that the unique features of this new *Aglaonema* are stable and reproduced true to type in successive generations.

SUMMARY OF THE INVENTION

The following traits have been repeatedly observed and are determined to be the unique characteristics of 'Sterling'. These characteristics in combination distinguish 'Sterling' as a new and distinct cultivar of *Aglaonema:*

1. Upright and outwardly arching plant form.
2. Vigorous growth habit.
3. Freely clumping habit; full, dense and bushy appearance.
4. Undulate lanceolate leaves with acuminate apices.
5. Leaves positioned roughly horizontally.
6. Unique leaf coloration; upper leaf surfaces lustrous silvery gray green-colored with sparse lighter silvery gray green-colored flecks and chevrons; lower leaf surfaces medium green-colored.
7. Green-colored leaf petioles with sparse and random pale yellow-colored spots and streaks.
8. Tolerant to low temperatures.

In side-by-side comparisons conducted by the Inventors in Chamrajpet, Bangalore, India, plants of the new *Aglaonema* differed from plants of the female parent, the *Aglaonema commutatum* cultivar Malay Lady, in the following characteristics:

1. Plants of the new *Aglaonema* were more outwardly arching than and not as upright as plants of the cultivar Malay Lady.
2. Plants of the new *Aglaonema* and the cultivar Malay Lady differed in leaf coloration as plants of the cultivar Malay Lady had dark green-colored leaves with silvery green-colored chevrons.
3. Plants of the new *Aglaonema* and the cultivar Malay Lady differed in leaf petiole coloration as plants of the cultivar Malay Lady had solid green-colored leaf petioles.

In side-by-side comparisons conducted by the Inventors in Chamrajpet, Bangalore, India, plants of the new *Aglaonema* differed from plants of the male parent, the *Aglaonema hybrida* selection KSG hybrid 85-22-1, in the following characteristics:

1. Plants of the new *Aglaonema* had a more uniform and outwardly arching growth habit than plants of the selection KSG hybrid 85-22-1.

2. Plants of the new *Aglaonema* were more freely clumping than plants of the selection KSG hybrid 85-22-1.
3. Plants of the new *Aglaonema* and the selection KSG hybrid 85-22-1 differed in leaf coloration as plants of the selection KSG hybrid 85-22-1 had dull green-colored leaves with large and random silvery gray-colored markings.
4. Plants of the new *Aglaonema* and the selection KSG hybrid 85-22-1 differed in leaf petiole coloration as plants of the selection KSG hybrid 85-22-1 had leaf petioles with more pale yellow spots and streaks.

Plants of the new *Aglaonema* can be compared to plants of the cultivar Moonshine, disclosed in U.S. Plant Pat. No. 10,574. In side-by-side comparisons conducted in Chamrajpet, Bangalore, India, plants of the new *Aglaonema* differed from plants of the *Aglaonema* cultivar Moonshine in the following characteristics:

1. Plants of the new *Aglaonema* were more vigorous and grew faster than plants of the cultivar Moonshine.
2. Leaves of plants of the new *Aglaonema* were narrower, longer and had more tapered apices than leaves of plants of the cultivar Moonshine.
3. Plants of the new *Aglaonema* and the cultivar Moonshine differed in leaf coloration as plants of the cultivar Moonshine had dull gray green-colored leaves without any flecking or chevrons.
4. Plants of the new *Aglaonema* and the cultivar Moonshine differed in leaf petiole coloration as plants of the cultivar Moonshine had solid dark green-colored leaf petioles.

Plants of the new *Aglaonema* can also be compared to plants of the cultivar Silver Queen, not patented. In side-by-side comparisons conducted in Chamrajpet, Bangalore, India, plants of the new *Aglaonema* differed from plants of the *Aglaonema* cultivar Silver Queen in the following characteristics:

1. Plants of the new *Aglaonema* were more outwardly arching than and not as upright as plants of the cultivar Silver Queen.
2. Plants of the new *Aglaonema* were more vigorous and were more freely clumping than plants of the cultivar Silver Queen.
3. Plants of the new *Aglaonema* and the cultivar Silver Queen differed in leaf coloration as plants of the cultivar Silver Queen had dark green and silvery gray green bi-colored leaves.
4. Plants of the new *Aglaonema* were more low temperature tolerant than plants of the cultivar Silver Queen.

BRIEF DESCRIPTION OF THE PHOTOGRAPH

The accompanying colored photograph illustrates the overall appearance of the new *Aglaonema,* showing the colors as true as it is reasonably possible to obtain in colored reproductions of this type. Colors in the photograph may differ slightly from the color values cited in the detailed botanical description which accurately describe the colors of the new *Aglaonema.*

The photograph comprises a side perspective view of a typical plant of 'Sterling'.

DETAILED BOTANICAL DESCRIPTION

The cultivar Sterling has not been observed under all possible environmental conditions. The phenotype may vary somewhat with variations in environment such as temperature and light intensity without, however, any variance in genotype.

The aforementioned photograph and following observations and measurements describe plants of the new *Aglaonema* that were grown in 25-cm containers, in Homestead, Fla., in a polypropylene-covered shadehouse with light levels about 2,500 foot-candles. During the production of the plants, temperatures ranged from 2 to 43° C. Plants used for the photograph and description were about 14 months from planting. Color references are made to The Royal Horticultural Society Colour Chart, 1995 Edition, except where general terms of ordinary dictionary significance are used.

Botanical classification: *Aglaonema hybrida* cultivar Sterling.

Parentage:

*Female, or seed, parent.*—*Aglaonema commutatum* cultivar Malay Lady, not patented.

*Male, or pollen, parent.*—Proprietary selection of *Aglaonema hybrida* identified as code number KSG hybrid 85-22-1, not patented.

Propagation:

*Type.*—By divisions.

*Time to initiate roots.*—Summer: About 18 to 20 days at 25 to 36° C. Winter: About 30 to 35 days at 15 to 28° C.

*Time to produce a rooted plant.*—Summer: About 30 to 35 days at 25 to 36° C. Winter: About 40 to 45 days at 15 to 28° C.

*Root description.*—Thick, fibrous, fleshy, and freely-branching.

Plant description:

*Plant form.*—Erect when young, becoming outwardly arching as leaves develop; inverted triangle, symmetrical and uniform.

*Vigor/growth rate.*—Vigorous; relatively rapid growth rate. Plant size appropriate for 25-cm containers.

*Growth habit.*—Freely clumping habit; plants typically produce about 18 offshoots per plant; full, dense and bushy appearance.

*Plant height.*—About 46 cm.

*Plant width* (*spread*).—About 44 cm.

*Stem description.*—Length: About 18 cm. Diameter: About 2.1 cm. Internode length: About 2.3 cm. Aspect: Upright. Strength: Good. Color: 146A.

*Foliage description.*—Appearance: Single; clasping. Length: About 23.2 cm. Width: About 6.75 cm. Shape: Lanceolate. Apex: Acuminate. Base: Obtuse to oblique. Margin: Entire; undulating. Orientation: Initially upright to roughly horizontal. Texture: Mostly smooth, slightly rugose; glabrous; thick and leathery. Veins: Slightly recessed on upper surface and prominent on lower surface. Venation pattern: Pinnate. Color: Developing and fully expanded leaves, upper surface: Close to 189A with occasional and random flecking and chevrons of close to 191A mostly along the primary lateral veins; lustrous. Developing and fully expanded leaves, lower surface: Close to 146A to 146B. Venation, upper and lower surfaces: Same as lamina. Petiole: Aspect: Erect to bent. Length: About 14.2 cm. Diameter, distal: About 7.5 mm. Diameter, proximal: About 2.5 mm. Wing length: About 10.5 cm. Wing diameter: About 3 mm. Color, petiole and wing: 146A to 146B with sparse and random spots and streaks, close to 4D.

Inflorescence description: Inflorescence development has not been observed on plants of the new *Aglaonema* grown under shadehouse production conditions.

Disease/pest resistance: Plants of the new *Aglaonema* have been observed to be resistant to pathogens common to *Aglaonema* such as *Xanthomomas* and *Phytophthora*. Plants of the new *Aglaonema* have not been observed to be resistant to pests and other pathogens common to *Aglaonema*.

Weather tolerance: Plants of the new *Aglaonema* have been observed to be tolerant to wind, rain and temperatures ranging from 2 to 43° C.

It is claimed:

1. A new and distinct cultivar of *Aglaonema* plant named 'Sterling', as illustrated and described.

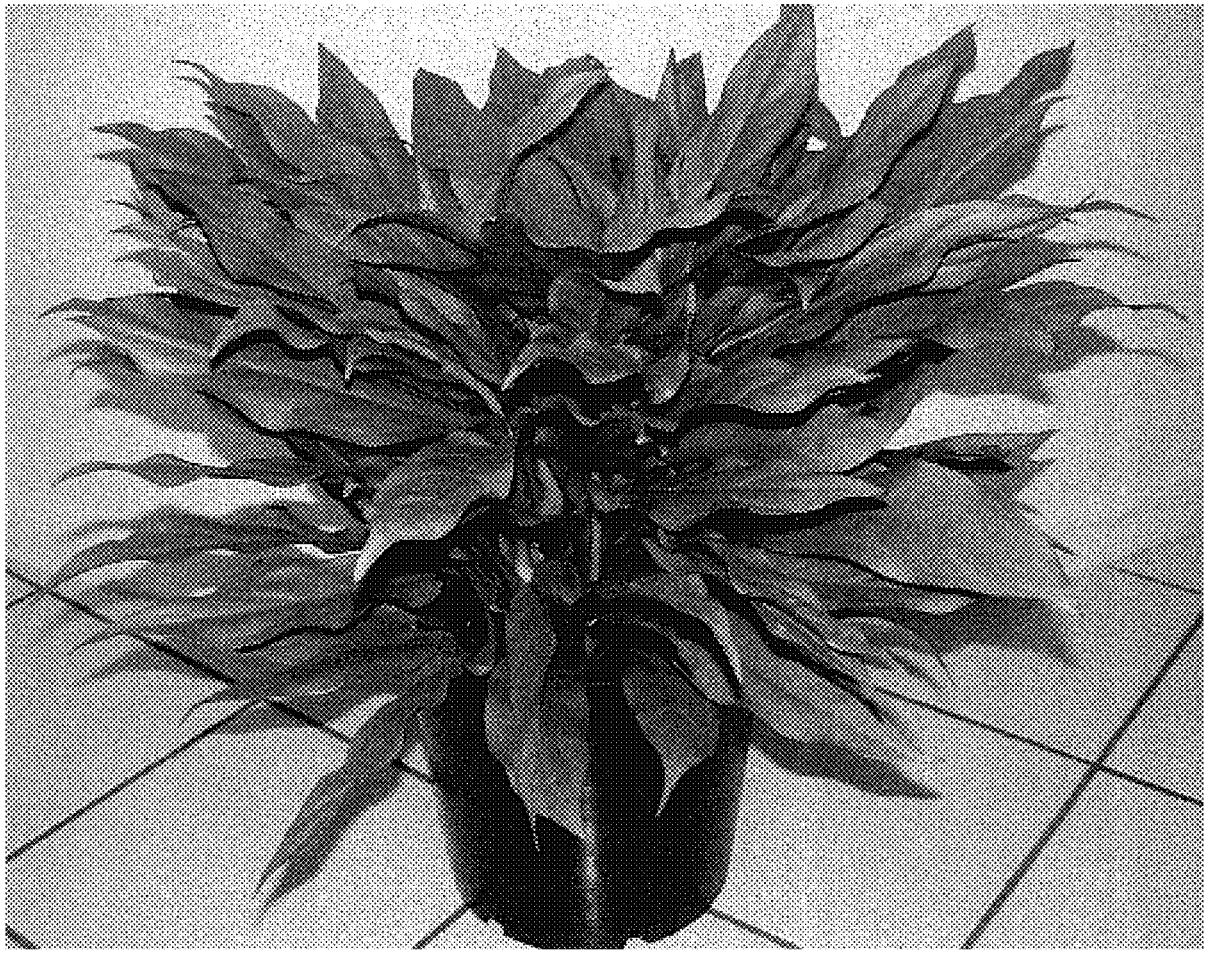

* * * * *